(12) United States Patent
Li et al.

(10) Patent No.: US 6,254,453 B1
(45) Date of Patent: Jul. 3, 2001

(54) OPTIMIZATION OF CHEMICAL MECHANICAL PROCESS BY DETECTION OF OXIDE/NITRIDE INTERFACE USING CLD SYSTEM

(75) Inventors: Leping Li, Poughkeepsie, NY (US); James A. Gilhooly, St. Albans; Clifford O. Morgan, III, Burlington, both of VT (US); Cong Wei, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/409,243

(22) Filed: Sep. 30, 1999

(51) Int. Cl.[7] .................................................. B26B 1/00
(52) U.S. Cl. ................................................ 451/8; 451/41
(58) Field of Search ............................... 451/8, 10, 11, 451/5, 36, 41, 60; 438/16, 7, 8, 104, 690, 691, 692, 693; 216/85; 422/52

(56) References Cited

U.S. PATENT DOCUMENTS

| | | | |
|---|---|---|---|
| 4,657,744 | * | 4/1987 | Howard .................................. 422/52 |
| 4,822,564 | * | 4/1989 | Howard .................................. 422/52 |
| 5,643,050 | | 7/1997 | Chen . |
| 5,663,797 | | 9/1997 | Sandhu . |
| 5,667,424 | | 9/1997 | Pan . |
| 5,695,660 | | 12/1997 | Litvak . |
| 5,747,380 | | 5/1998 | Yu et al. . |
| 5,838,448 | | 11/1998 | Aiyer et al. . |
| 5,851,135 | | 12/1998 | Sandhu et al. . |
| 6,096,267 | * | 8/2000 | Kishkovich et al. .................. 422/52 |

OTHER PUBLICATIONS

"End–Point Detection of Chemical/Mechanical Polishing of Circuitized Multilayer Substrates" IBM Technical Disclosure Bulletin vol. 34, No. 4b, Sep. 1991.

\* cited by examiner

Primary Examiner—M. Rachuba
(74) Attorney, Agent, or Firm—Venable et al.; Jay H. Anderson

(57) ABSTRACT

A method is provided to optimize the chemical mechanical planarization process of wafers having a target removal layer and a stop layer. A slurry is added to a polishing table which includes a polishing pad and a platen adapted for rotation; a portion of the slurry is allowed to engage an interface between the polishing pad and the wafer. A gaseous sample is continuously extracted from the slurry; the gaseous sample includes a reactant product created when the polishing pad engages the stop layer. The gaseous sample is introduced into a reactant product detector. A first time is determined, corresponding to an initial detection of the reactant product in the slurry, thereby creating a first reference point. A second time is determined, corresponding to the detection of a maximum volume of the reactant in said slurry, thereby creating a second reference point. The first and second reference points are then processed to obtain a signal, wherein the signal reflects the uniformity of removal of the layer containing the reactant product.

6 Claims, 5 Drawing Sheets

OPTIMIZATION OF CHEMICAL MECHANICAL PROCESS BY DETECTION OF OXIDE/NITRIDE INTERFACE USING CLD SYSTEM

This invention is related to the following co-pending U.S. Patent Applications:

Ser. No. 09/073,604 entitled "Indirect End Point Detection by Chemical Reaction and Chemiluminescence";

Ser. No. 09/073,606 entitled "End Point Detection by Chemical Reaction and Photoionization";

Ser. No. 09/129,003 entitled "Improved Chemical-Mechanical Polishing End Point Process Control"; and Ser. No. 09/129,102 entitled "Probe for Slurry Gas Sampling," each of which is incorporated herein by reference.

FIELD OF THE INVENTION

This invention relates to chemical mechanical planarization ("CMP") processes and, more particularly, improvements with the monitoring of the CMP process in connection with the removal of silicon dioxide films with stops on layers containing silicon nitride/silicon dioxide.

BACKGROUND OF THE INVENTION

The manufacture of the wafers for integrated circuits involves the formation of a series of layers or films upon a silicon wafer. In the typical manufacturing process, a wafer undergoes a photo resist step followed by photo lithography. The wafer is then etched, stripped and then subjected to a diffusion step. The planarization process is then used to planarize the surface of the wafer before the wafer is subjected to repeated iterations of these steps which build multiple layers on the wafer. CMP has been described as "wet sanding" the surface of the wafer and, the object of the planarization process is to achieve a highly uniform planar surface on the wafer without excessive removal or an insufficient removal of the film.

It is desirable to have each layer on the wafer extremely flat or planar before the creation of each successive layer mainly to improve the lithography and enable better control of the shrinking dimension. Before the incorporation of CMP processes, the topography of the wafer is irregular and, as a result, a lithographic image formed on the surface of the wafer may be out of focus. The lack of focus will interfere with subsequent etching steps which results in a larger uncertainty of process control and forces a larger ground rule.

The typical apparatus used in the CMP process includes a carrier which holds a wafer. This assembly is rotated and pushed down with the surface of the wafer which is to be polished oriented toward an abrasive pad. The abrasive pad is mounted on a platen which rotates on a different axis than the carrier. Typically, a water based slurry containing uniformly distributed and suspended small abrasive particles is introduced to the top surface of the rotating pad which contributes mechanical and/or chemical elements to the process. When the CMP process is directed to the removal of oxide layer on a wafer, the slurry is typically made of a water-based solution containing fumed silica with its pH between 10 and 11, adjusted by KOH. In contrast, when the slurry is intended for the polishing of a metallic layer, the slurry will typically contain oxidizers and have a low pH (0.5 to 4). New slurry is continuously introduced to the process as old slurry is removed. The old slurry will contain the abraded particles of both the pad and the wafer and end products of the chemical reaction. Following the CMP process the wafer is buffed to remove any slurry and cleaned to provide a smooth final finish to the wafer.

The CMP process is used for the planarization of both dielectric and metallic layers. The CMP process when applied to surfaces comprising metallic layers involves a chemical reaction at the surface of the wafer which leaves the surface more susceptible to mechanical abrasion by the particles suspended in the slurry. However, mechanical abrasive action dominates when the CMP process is directed toward oxide polishing. Notwithstanding, it has been found that the removal of oxide layers containing silicon nitride involves significant mechanical and chemical activity. Mechanical abrasive action of a silicon nitride layer creates a large surface area due to the numerous silicon nitride particles created in the process and therefore the chemical reaction yield is enhanced. At low pH the main product is $NH_4+$ and at high pH it exits mainly as $NH_3$.

There are a wide number of variables which can influence the rate and uniformity of the planarization operation. Mechanical variables involved in the process include the rotational speeds of the platen and carrier, the back pressure applied to the pad, the profile of the pad and carrier and the downward force applied to the platen. Further, the various components used in the process contribute to yet additional variables in the operation. Typically, the polishing pad on the platen is made of polyurethane and the surface is much rougher than the typical wafer being polished. Variation in the polishing pads or other consumables used in the process can significantly alter the rate of removal of layers on a wafer. In addition to the mechanical control parameters, the characteristics of the slurry add a number of additional variables, including the particle size distribution, temperature, pH and its rate of introduction. The CMP process itself is dynamic which further contributes to difficulties in precisely controlling the process and achieving repeatable results.

The total polishing time will depend on the initial film thickness and the film removal rate. The removal rate is dependent on the various process parameters identified above. To improve throughput, material removal rate can be maximized. Removal rate and removal rate uniformity across a wafer are also strong functions of downforce, platen speed, pad structure and slurry chemistry. Unfortunately, optimizing parameters for maximum removal rate is in conflict with optimized planarization. Thus, processes vary by application and the priority of the desired responses. During the development of a new device, considerable time is expended selecting the optimal mechanical parameters for the CMP process including the polishing pad features, the slurry characteristics, and the speeds and force between the platen and carrier. In the past this process has heavily relied upon experimental data relating to uniformity and film removal rate.

The output of the CMP process is planarized/polished wafers. Typical output characteristics being measured and monitored are the amount of material removed and its removal rate, within-wafer non-uniformity of material removed, wafer-to-wafer non-uniformity of the removal rate, the degree of planarization, as well as surface defects and contamination. The difference between pre- and post-CMP measurements provides information on the change caused by the process, such as the amount removed and the removal non-uniformity. Within-wafer non-uniformity is commonly measured as a standard deviation of the thickness removal measurements expressed as a percentage of the average thickness removed. Wafer-to-wafer non-uniformity is a standard deviation of removal rate for a number of wafers expressed as a percent of the average removal rate. Higher down-force reduces polish time and hence, increases the throughput but may adversely affect planarization and possibly non-uniformity.

In view of the numerous variables which effect the CMP process, optimizing the control of the process without an effective endpoint detection system presents difficulties. Merely attempting to precisely repeat operating conditions based upon historical results does not achieve reliable or satisfactory results. Removal of the wafer from the polishing table for periodic inspection and analysis significantly reduces the throughput and can introduce further variables into the process. In response to the need to monitor and control the progress of the CMP process, and more particularly, to accurately identify the endpoint of the process, a number of in situ techniques have been developed to monitor the rate of removal. For layers having metal components, a number of techniques have been used which either measure motor current changes or the frequency shift of a resonant circuit due to inductance change. With particular respect to the measurement of dielectric layers where the aforesaid techniques are ineffective, efforts have included (1) measuring the changes in frictional forces between the pad and the wafer by more sensitive means, (2) providing a window through the polishing pad or from the back of the wafer and, using an infrared light source, and then measuring changes in optical properties of the film being removed, and (3) sensing the acoustical changes in the process exhibited by different layers.

At present shallow trench isolation CMP requires the complete exposure of silicon nitride at the interface of the top two films without excessive removal of silicon nitride. BPSG CMP usually stops somewhere at the interface when the silicon nitride layer is partially exposed.

There is a continuing need for improved methods and devices for the in situ monitoring of the CMP process. In particular, for shallow trench isolation CMP process optimization, with any adjustment of any of the parameters, the goal is to stop the wafer polishing process at a time when all the nitride area has just been cleared. The identification of this point is very difficult because each change of the multiple factors which effect the CMP process will change the optimal stop time. Preferably detection of changes in process conditions should have a high degree of sensitivity and a rapid response time, preferably less than 1 or 2 seconds.

SUMMARY OF THE INVENTION

The present invention is directed at a new method and device for the in situ monitoring of the CMP process of wafer layers containing silicon nitride. The present invention allows one to rapidly determine when the removal of a layer containing nitride occurs which can be used very effectively to calculate the endpoint regardless of changes made to the process variables which can influence the CMP process. The ability to quickly and accurately detect the endpoint allows for the optimization of a CMP process which can increase device yield, reduce raw process cost and increase throughput. Real time feedback as provided by the invention is particularly valuable because it enables a manufacturer to alter process variables during the CMP process in order to optimize a new process and speed up development of new devices. In situ, real time monitoring also can provide information relating to removal rate or time changes which may enable a manufacturer to discover problems associated with incoming wafers and take corrective action or to arrest further processing. According to the invention, the ammonia formed during the removal of nitride layers is extracted from the slurry and mixed with a carrier gas. The ammonia is then oxidized to form nitric oxide (NO) according to the Oswald process. Nitric oxide is then directed to a CLD analyzer which can make detections of NO at very low levels. The technique is based upon the chemiluminescent reaction between ozone and nitric oxide (NO) yielding excited state nitrogen dioxide ($NO_2^*$) and oxygen. The photons emitted from $NO_2^*$ are measured by a sensitive photon detector and its associated amplification electronics. Existing commercially available analyzers, principally designed for environmental applications, can rapidly and with a high degree of sensitivity detect the presence of nitric oxide at levels below parts per billion. The signal generated by the detector is then processed and used to monitor the CMP process. Thus, the present invention, by continuously monitoring for certain chemical constituents of the CMP process which have been extracted from the slurry, allows the endpoint system to determine the exposure or disappearance of the nitride-containing film during the CMP process. If an unanticipated event is detected, as reflected by a change or aberration from the expected signal, either physical or chemical process parameters can be adjusted in order to respond to the event. For example, the interruption of the slurry supply can cause an endpoint trace characterized by the absence of a "rising" signal. Double deposition of the top film may be manifested n an endpoint trace signal by a "rising signal" having a duration twice the anticipated time. Furthermore, the existence of widely fluctuating removal rates can provide the operator with an indication of a potential problem in the process which can then be appropriately addressed.

DETAILED DESCRIPTION

Figure 1:
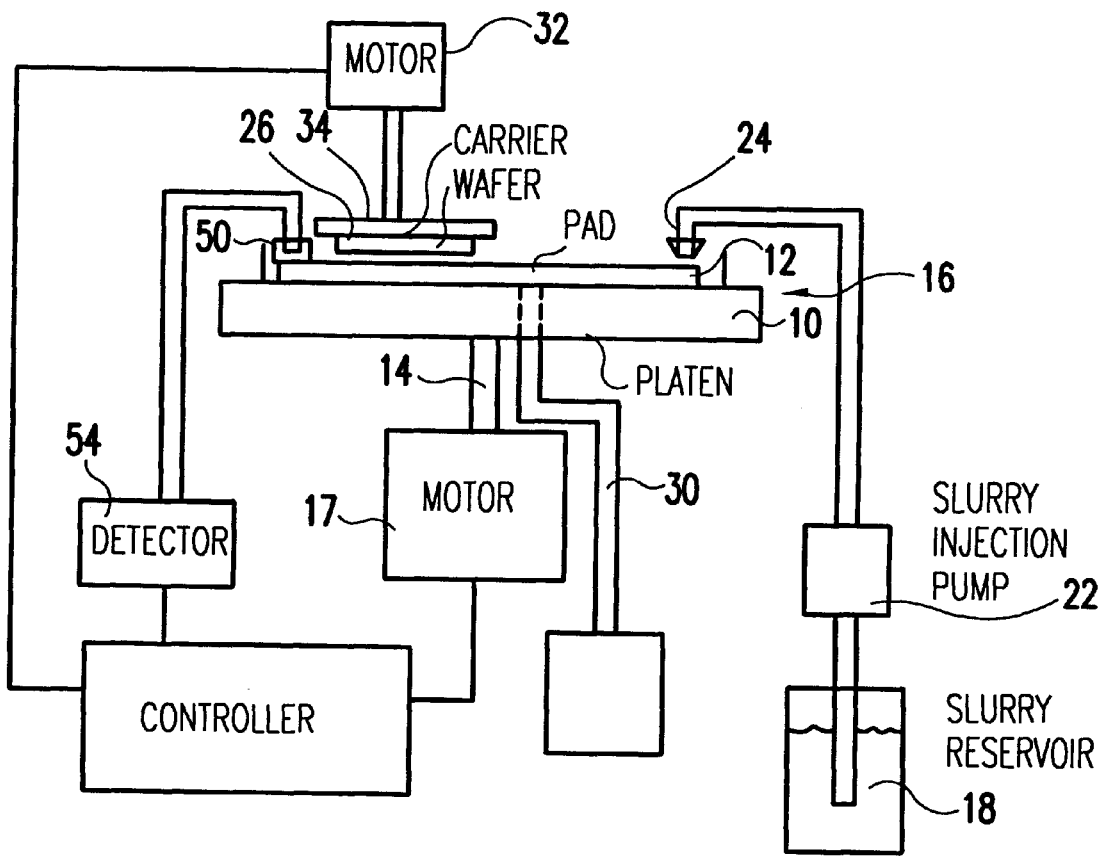
FIG. 1 is a schematic diagram of a CMP assembly used with the present invention.
Figure 2:
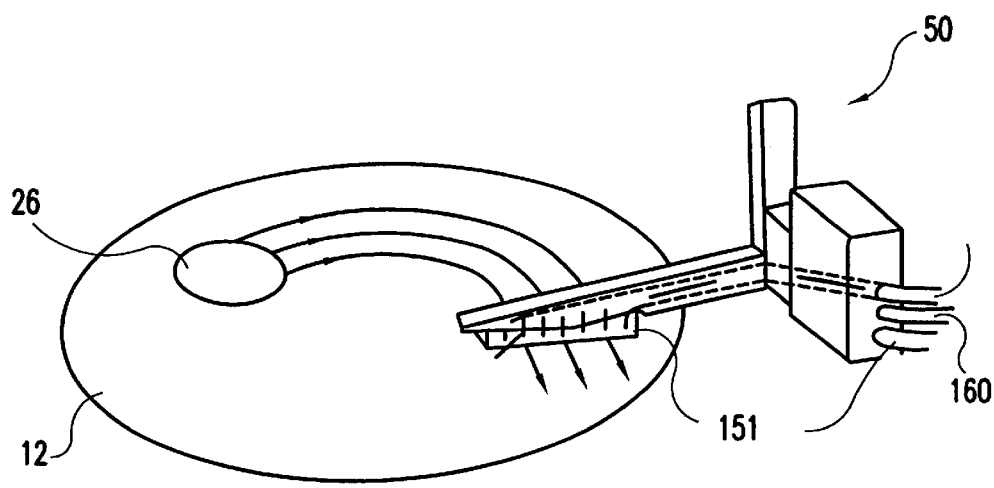
FIG. 2 is a schematic representation of an extraction unit and its relationship with the carrier and platen.

Now referring to FIG. 1 a device used in connection with the CMP processing of wafers, includes a platen 10 on which is secured an abrasive polishing pad 12 which together form a polishing table 16. Platen 10 is rotated at a constant speed about a central axis 14 by motor 17. A slurry reservoir 18 containing a polishing slurry is continuously introduced on to polishing pad 12 pad via injection pump 22 through nozzle 24. Slurry is introduced to the polishing pad in a manner which allows for a uniform distribution and which covers the entire area of the wafer 26 where it engages the pad. Slurry is also continuously removed from the pad at the periphery of the platen due to centrifugal force. As best seen in FIG. 2, during CMP a probe head 151 of the extraction unit 50 sits on the slurry soaked pad 12 with its separation membrane 153 covered by a thin film of slurry. The probe allows for the extraction of NH₃ gas from the aqueous slurry which contains ammonia in the liquid phase. Any residual slurry is later removed from the wafer by high pressure water spray at the end of the CMP process. Referring back to FIG. 1, motor 32 rotates a carrier 34 and applies a downward force causing the wafer to engage polishing pad 12.

Figure 3:
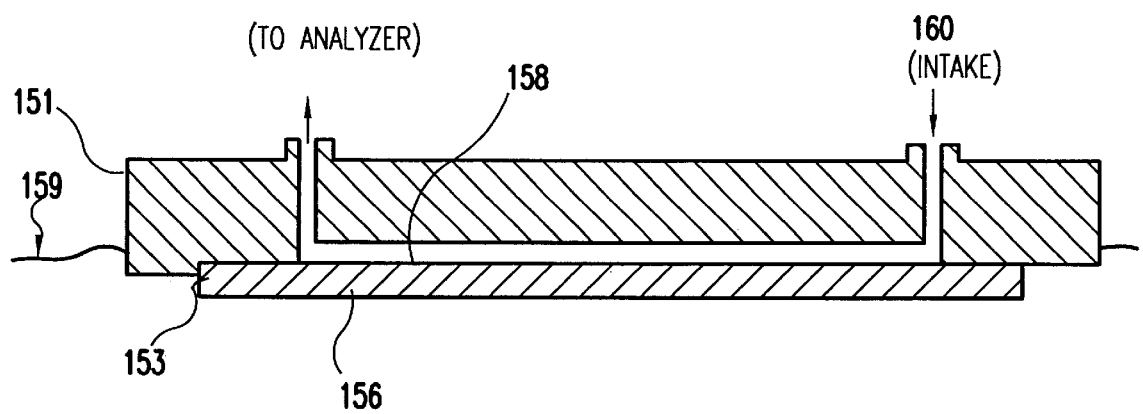
FIG. 3 is a side sectional view of the head of an extraction unit used with the present invention.

FIG. 3 depicts the probe head 151 in contact with the slurry. Probe head 151 contains a semipermeable hydrophobic membrane 153 which separates an internal conduit 155 from the external environment. The external surface 156 contacts the slurry, which is under a pressure of 1 atmosphere or ambient conditions. On the opposite internal surface 158 of membrane 153, or within the internal conduit 155, the pressure is maintained slightly less than 1 atmosphere by a vacuum pump located downstream of the analyzer. A clean dry carrier gas is introduced to the system at intake manifold 160 and it mixes with sample gas extracted from the slurry behind membrane 153. The sample gas exits the through portal 162 where it is then transported to the analyzer. The difference in pressure behind the semipermeable membrane allows for the easy extraction of ammonia in the gas phase out of the slurry while the introduction of the carrier gas lowers the water vapor in the sample. Removing the water vapor mitigates the formation of water particles sticking to the surface along the conduit which directs the sample gas to the analyzer and enables a rapid transportation of the extracted sample gas to the chemical analyzer. Extraction units which can be used in connection with the present invention are further described in a co-pending U. S. application Ser. No. 09/129,102 entitled "Probe for Slurry Gas Sampling" and that application is incorporated by reference herein.

Figure 4:
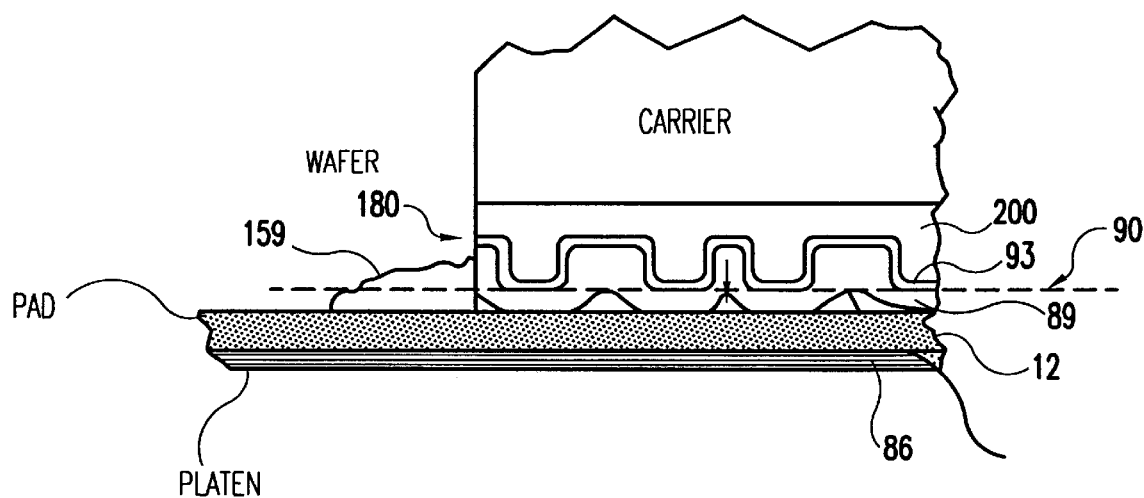
FIG. 4 is a side sectional view of the interface between a polysilcon wafer, and an abrasive polishing pad.

FIG. 4 depicts a cross section of a wafer substrate 200 on a polishing table which is undergoing the CMP process. Polishing pad 12 is in engagement with surface 86 of an oxide layer 89. When the polishing process reaches the interface 90 between the oxide layer 89 and the silicon nitride/silicon dioxide layer 93, a detectable amount of ammonia is created and introduced to the slurry. This interface is represented as t1 in FIG. 6. As the polishing process continues, the process will reach a point of maximum removal of the nitride layer which is represented by t2 in FIG. 4. A rapid decrease in the nitride signal, identified as the signal between t2 and t3, indicates the disappearance of silicon nitride reflecting a decrease in total exposed area on the wafer surface. When the polishing pad begins to abrade the surface of the wafer containing silicon nitride, a small amount of ammonia is formed which goes into solution within the slurry. It has been found that the removal of layers containing silicon nitride using an alkaline slurry during the CMP process creates small but appreciable amounts of ammonia. See pending U.S. application Ser. No. 09/073,605 entitled "Endpoint Detection by Chemical Reaction and Photoionization" which is hereby incorporated herein by reference. When polishing silicon nitride, the following reaction occurs:

$$Si_3N_4 + 6KOH + 3H_2O \rightarrow 3K_2SiO_3 + 4NH_3$$

Ammonia formed in the reaction can be readily extracted from the aqueous slurry when the slurry has a high pH (greater than 10).

In aqueous solutions containing a strong base, ammonia is evolved and the following reaction is driven to the right:

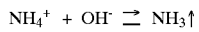

It is believed that the amount of ammonia generated is enhanced in the CMP process because of the large surface area caused by the polishing action.

Figure 5:
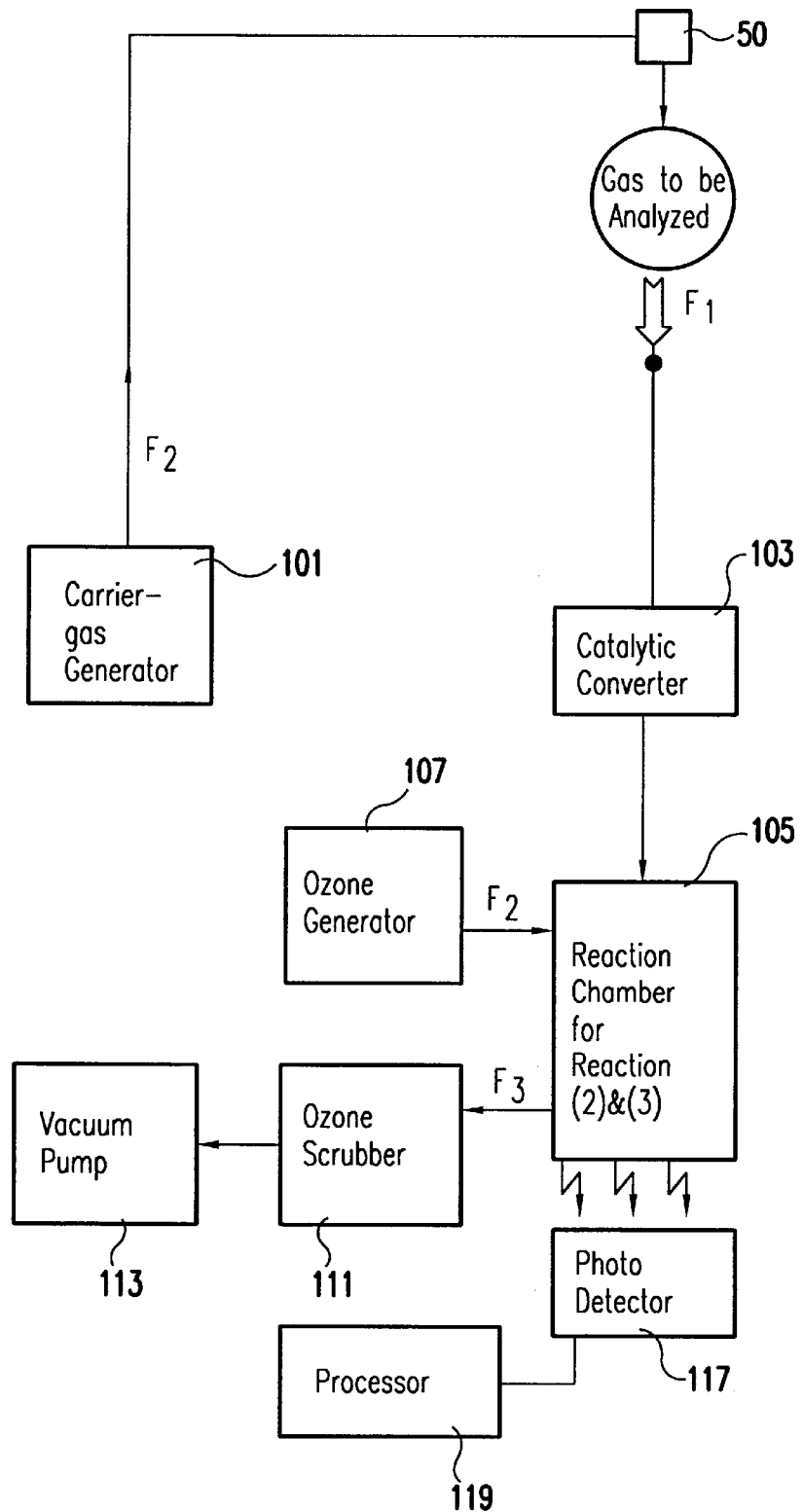
FIG. 5 is a schematic diagram of a detector according to the preferred embodiment of the invention.

Now referring to FIG. 5, the clean, dry carrier gas is introduced to the system downstream of the extraction unit 50 at a reduced pressure which enhances the transport of ammonia from the slurry into the gas stream. The carrier gas is conditioned to be free of H₂O, NO, NO₂, NH₃ and is generally referred to as dry and clean. Mixing the extracted ammonia gas with the dry and clean carrier gas helps reduce the loss of sample gas during its transportation to the analyzer due to adsorption. It also increases the travel speed and prevents background noise due to the presence of adsorbed molecules (H₂O and NH₃). In view of the small sample size of the gas available for detection, and its further dilution by the carrier gas, the concentration of ammonia available for testing generated from the polishing of the layer containing nitride is typically small and in the amount of only a few parts per billion. Because the concentration of the target gas available for detection is very low, a highly sensitive detection scheme is necessary.

In the preferred embodiment, the presence of ammonia gas is detected using NO chemiluminescence. The sample containing ammonia is first catalytically converted to nitric oxide (NO) at an elevated temperature. The conversion, known as the Oswald process, proceeds according to the following reaction:

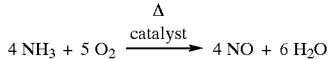

The resulting NO molecules are then mixed and reacted with ozone molecules in reaction chamber 105. The ozone molecules are generated in situ by corona discharge of either air or oxygen in ozone generator 107. The reaction product contains NO₂* an unstable molecule and a certain percentage of the NO₂* present will decay emitting photons. As the molecule makes the transition from the exited state to a ground state, photons emitted can be detected using a photo multiplier tube (PMT). The light emitted as the molecules transfer from the excited state to the ground state is in a broad band at approximately 1200 nm. Thus sample gas from the extraction unit 50 is introduced to catalytic converter 103 where ammonia is converted to nitric oxide. Ozone is provided from ozone generator 107 and combined with the nitric oxide in reaction chamber 105. A vacuum pump 133 draws the gas through the system. A detector which can be employed in accordance with the teachings of the present invention is more fully disclosed in co-pending U.S. application Ser. No. 09/129,003 entitled "Chemiluminescence Detection Apparatus" which is incorporated by reference herein. Data from photo detector 117 is then fed into a processor 119 which processes the data and provides an output to a process controller in response to the levels of nitric oxide present.

Figure 6:
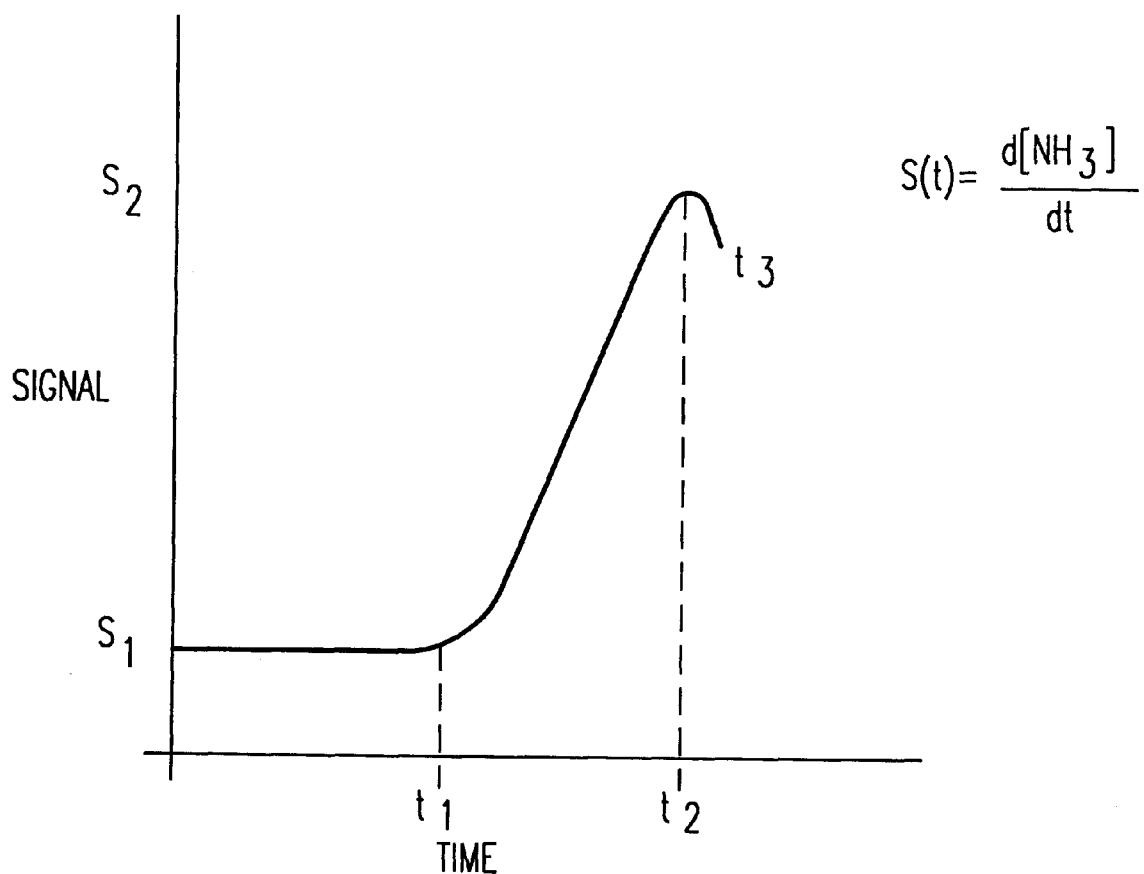
FIG. 6 is a graph depicting a signal which correlates to the removal of a nitride layer plotted against time.

Now referring to FIG. 6, the output of the photo detector 117 is a signal S which can plotted over time. The derivative of the signal can be calculated to determine the rate of removal and to easily identify the peak or the time reflecting the substantially complete removal of the layer containing silicone nitride according to the following equation:

$$s = \frac{d[NH_3]}{dt}$$

The level of nitric oxide closely correlates with the volume of ammonia concentration in the slurry. In the preferred embodiment, the derivative is calculated to determine the rate of change of the removal of the layer containing silicon nitride.. Accordingly, the signal will reflect real time feedback relating to the CMP process as it progresses through an oxide layer and then into a layer of the wafer containing silicon nitride. The detection of nitric oxide accordingly allows for a precise identification of the time in the process when the removal of the nitride layer on the wafer has been initiated and when the layer has been substantially cleared. Further, the signal also reflects the rate of removal of the nitride layer. The output of this signal trace analysis can be used to determine the precise stop time for the polish operation.

The system as described can be used to solve optimization issues in the CMP process as well as determining the endpoint because it is capable of providing a consistent stop time for each wafer polishing step regardless of adjustments or changes to process parameters. Furthermore, data from the signal provides a trace record providing information related to the overall polishing uniformity, the rate of removal and the rate change. In this regard, the polishing uniformity can be correlated to the relative differences between two well-defined reference points provided by the signal. A first reference point t1 corresponds to the onset of the removal of the layer containing nitride and a second reference point t2 may reflect the maximum nitride removal rate. If the incoming wafers have similar film thickness distributions, then the polish process will yield a steep change between the reference points, reflecting a better polishing uniformity.

The present invention also allows for the rapid optimization of process variables during experimentation on a new device which in the past had been time-consuming. The use of the present endpoint detection system can accordingly serve to significantly reduce the CMP process development cycle for a particular device and allow for the quick optimization of the respective CMP parameters. Due to its extremely high detection sensitivity (sub ppb), this technique works even for wafers with very small pattern factor product wafers.

Although a specific embodiment has been described and illustrated herein, those having skill in the art will appreciate that there are additional arrangements and applications employing the invention which may be substituted for the specific disclosure as described herein. For example, the present detection device discloses a chemiluminescent analyzer; however it is contemplated that other detection techniques which provide signals containing information relative to the rate of nitride removal from the wafer may also be employed. Having thus described the present invention and its preferred embodiment in detail, it will be readily apparent to those skilled in the art that further modifications to the invention may be made without departing from the spirit and scope of the invention as presently claimed.

We claim:

1. A method to optimize the chemical mechanical planarization process of wafers having a target removal layer and a stop layer comprising, adding slurry to a polishing table, said polishing table comprising a polishing pad and a platen adapted for rotation, allowing a portion of said slurry to engage an interface between said polishing pad and said wafer, continuously extracting a gaseous sample from said slurry, said gaseous sample further comprising a reactant product created when said polishing pad engages said stop layer, introducing the said gaseous sample to a reactant product detector, determining a first time corresponding to an initial detection of said reactant product in said slurry thereby creating a first reference point, determining a second time corresponding to the detection of a maximum volume of said reactant in said slurry, thereby creating a second reference point, and processing said first and said second reference points to result in a signal, wherein said signal reflects the uniformity of removal of said layer containing said reactant product.

2. The method as recited in claim 1 wherein said signal is transmitted to a CMP process controller which controls CMP process variables.

3. The method recited in claim 2 wherein said CMP process variables comprise the speed of rotation of the platen and carrier, the force between the wafer and the pad, the temperature of the slurry, and the rate of introduction of slurry.

4. The process as recited in claim 1 wherein said reactant product detector comprises a chemiluminescence analyzer.

5. The method as recited in claim 1 wherein said stop layer comprises silicon nitride and said reactant product comprises ammonia.

6. A method to monitor the mechanical chemical polishing process of a polysilicon wafer having a stop layer comprised of silicon nitride, said method comprising continuously extracting gas from a polishing slurry in contact with said wafer to provide a gas sample, continuously introducing said sample to a catalyst wherein any ammonia gas within said sample mixture will react with said oxygen to form nitric oxide, introducing said sample to a chemiluminescent analyzer wherein said analyzer provides a signal in response to the volume of nitric oxide in said sample, continuously comparing said signal over a time period, and processing said signal to determine changes in the volume of nitric oxide over said time period wherein said signal provides data reflecting the existence and rate of removal of said layer containing silicon nitride.

* * * * *